United States Patent
Sarrafzadeh et al.

(10) Patent No.: US 10,402,540 B2
(45) Date of Patent: Sep. 3, 2019

(54) TASK OPTIMIZATION IN REMOTE HEALTH MONITORING SYSTEMS

(71) Applicant: THE REGENTS OF THE UNIVERSITY OF CALIFORNIA, Oakland, CA (US)

(72) Inventors: Majid Sarrafzadeh, Anaheim, CA (US); Myung-Kyung Suh, Los Angeles, CA (US); Mars Lan, Los Angeles, CA (US); Hassan Ghasemzadeh, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 920 days.

(21) Appl. No.: 14/424,941

(22) PCT Filed: Aug. 27, 2013

(86) PCT No.: PCT/US2013/056901
§ 371 (c)(1),
(2) Date: Feb. 27, 2015

(87) PCT Pub. No.: WO2014/036032
PCT Pub. Date: Mar. 6, 2014

(65) Prior Publication Data
US 2015/0234997 A1     Aug. 20, 2015

Related U.S. Application Data

(60) Provisional application No. 61/694,183, filed on Aug. 28, 2012.

(51) Int. Cl.
*G06Q 50/00* (2012.01)
*G06F 19/00* (2018.01)
(Continued)

(52) U.S. Cl.
CPC ......... *G06F 19/3418* (2013.01); *G06N 5/025* (2013.01); *G16H 50/20* (2018.01);
(Continued)

(58) Field of Classification Search
CPC .............................. G06Q 50/00; G06F 19/345
See application file for complete search history.

(56) References Cited

U.S. PATENT DOCUMENTS 6,134,555 A    10/2000   Chadha et al.
6,574,583 B1    6/2003   Brossette et al.
(Continued)

FOREIGN PATENT DOCUMENTS

EP     1677668 B1 *   7/2010

OTHER PUBLICATIONS

Google patents search history, Dec. 18, 2017.*
(Continued)

*Primary Examiner* — Dilek B Cobanoglu
(74) *Attorney, Agent, or Firm* — Foley & Lardner LLP; Cliff Z. Liu

(57) ABSTRACT

Systems, methods, and devices are disclosed that monitor the health status of patients. Dynamic task management functions apply data analytics to discretize continuous data values from monitored patients, and apply association rule mining techniques to prioritized required user tasks, to minimize the number of daily action items required by patients. The remaining action items maximize information gain, thereby improving the overall level of patient adherence and satisfaction without losing health monitoring effectiveness.

23 Claims, 9 Drawing Sheets

(51) Int. Cl.
  *G06N 5/02*    (2006.01)
  *G16H 50/20*   (2018.01)
  *G16H 50/30*   (2018.01)
  *G16H 10/20*       (2018.01)

(52) U.S. Cl.
  CPC ....... *G16H 50/30* (2018.01); *F04C 2270/041* (2013.01); *G16H 10/20* (2018.01)

(56) References Cited

U.S. PATENT DOCUMENTS

| | | | | |
|---|---|---|---|---|
| 8,326,652 | B2* | 12/2012 | Sweeney | A61B 5/0031 |
| | | | | 705/3 |
| 8,740,789 | B2* | 6/2014 | Brockway | A61B 5/00 |
| | | | | 128/920 |
| 2002/0038307 | A1 | 3/2002 | Obradovic et al. | |
| 2006/0052945 | A1 | 3/2006 | Rabinowitz et al. | |
| 2010/0318155 | A1 | 12/2010 | Mahajan et al. | |
| 2011/0010202 | A1 | 1/2011 | Neale | |
| 2011/0282815 | A1 | 11/2011 | Thomas | |
| 2012/0109859 | A1 | 5/2012 | Fokoue et al. | |

OTHER PUBLICATIONS

Google patents search, Mar. 27, 2019 (Year: 2019).*
International Search Report for International Application No. PCT/US2013/056901 dated Dec. 9, 2013.
Extended European Search Report and Opinion for European Application No. 13833987.4 dated May 18, 2017, 8 pages.

* cited by examiner

| MONITORED ITEM | POSSIBLE VALUES |
|---|---|
| BLOOD GLUCOSE VALUE | 80 – 200 MG/DL |
| Q1: HAVE YOU HAD ANY BLOOD SUGAR READINGS < 80 OR > 200? | YES / NO |
| Q2: HAVE YOU MISSED DOSES OF YOUR MEDICATION? | YES / NO |
| Q3: TODAY, IS YOUR HEALTH GOOD, FAIR, OR POOR? | GOOD / FAIR / POOR |
| Q4: COMPARED TO YESTERDAY, ARE YOU FEELING BETTER, ABOUT THE SAME, OR WORSE? | BETTER / SAME / WORSE |

| | BLOOD GLUCOSE (MG/DL) | | | | | |
|---|---|---|---|---|---|---|
| | LEVEL 1 | | LEVEL 2 | | LEVEL 3 | |
| TIME | MEAN | STDEV | MEAN | STDEV | MEAN | STDEV |
| 00:00:00 -> 08:29:59 (T1) | 124.9 | 28.9 | 213.2 | 53.35 | 426.4 | 16.24 |
| 08:30:00 -> 15:09:45 (T2) | 133.6 | 27.52 | 187.1 | 60.65 | 273.8 | 138.6 |
| 15:09:46 -> 23:59:59 (T3) | 139.9 | 38.69 | 215.5 | 68.41 | 438.3 | 161.1 |

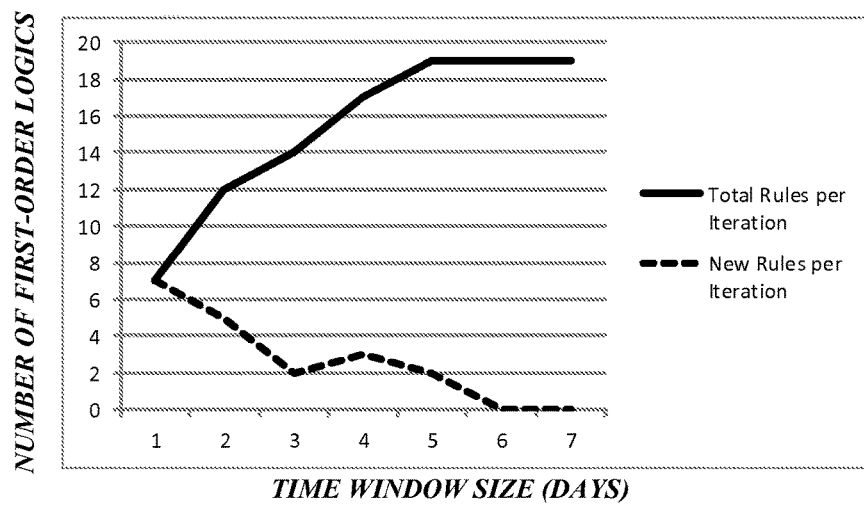

| IF | THEN | PROB |
|---|---|---|
| ANSWER OF Q3 ON DAY 1 IS (GOOD OR FAIR) AND ANSWER OF Q4 ON DAY 2 IS (BETTER OR SAME) | ANSWER OF Q3 ON DAY 2 IS (GOOD OR FAIR) | 0.9970 |
| ANSWER OF Q3 ON DAY 1 IS (GOOD OR FAIR) AND ANSWER OF Q4 ON DAY 2 IS (BETTER OR SAME) AND ANSWER OF Q4 ON DAY 3 IS (GOOD OR FAIR) | ANSWER OF Q3 ON DAY 3 IS (GOOD OR FAIR) | 0.9990 |
| ANSWER OF Q3 ON DAY 1 IS POOR | - ANSWER OF Q3 ON DAY 2 IS POOR<br>- ANSWER OF Q3 ON DAY 3 IS POOR<br>- ANSWER OF Q4 ON DAY 2 IS WORSE<br>- BLOOD GLUCOSE IS > 372 BEFORE 8:30 AM ON DAY 1<br>- BLOOD GLUCOSE IS ABOVE 372 BEFORE 8:30 AM ON DAY 2<br>- BLOOD GLUCOSE IS ABOVE 372 BEFORE 8:30 AM ON DAY 3 | 0.8889 |
| ANSWER OF Q4 ON DAY 1 IS (BETTER OR SAME) | ANSWER OF Q3 ON DAY 1 IS (GOOD OR FAIR) | 0.9961 |
| ANSWER OF Q4 ON DAY 1 IS (BETTER OR SAME) AND ANSWER OF Q4 ON DAY 2 IS (BETTER OR SAME) | ANSWER OF Q3 ON DAY 1 IS (GOOD OR FAIR) | 0.9980 |
| BLOOD GLUCOSE < 372 BEFORE 8:30 AM ON DAY 1 AND ANSWER OF Q4 ON DAY 2 IS (BETTER OR SAME) AND ANSWER OF Q4 ON DAY 3 IS (BETTER OR SAME) | ANSWER OF Q3 ON DAY 2 IS (GOOD OR FAIR) | 0.9990 |
| BLOOD GLUCOSE IS ABOVE 166 AND BELOW 372 BEFORE 8:30 AM ON DAY 1 | NO MULTIPLE MEASUREMENT BEFORE 8:30 AM ON DAY 1 | 0.9964 |

*Fig.6.*

TASK OPTIMIZATION IN REMOTE HEALTH MONITORING SYSTEMS

CROSS-REFERENCE(S) TO RELATED APPLICATION(S)

This application is a National Stage Entry of PCT/US2013/056901, filed Aug. 27, 2013, which claims the benefit of U.S. Provisional Application No. 61/694,183, filed Aug. 28, 2012, the entire disclosure of which is hereby incorporated herein by reference for all purposes.

STATEMENT OF GOVERNMENT LICENSE RIGHTS

This invention was made with Government support under Grant Number LM007356, awarded by the National Institutes of Health. The Government has certain rights in the invention.

BACKGROUND

Chronic diseases such as heart failure, diabetes, cancer, and stroke are the leading causes of death and disability in the United States. More than 70% of deaths among Americans are caused by chronic diseases and more than 133 million Americans, or about 1 out of 2 adults, have at least one chronic disease. Costs of chronic illness are also hard to neglect. In the United States, heart failure cost $39.2 billion in 2010, and diabetes cost $174 billion in 2007. Early diagnosis and treatment can improve quality of life and life expectancy for people with chronic diseases. Treatment usually involves lifestyle changes such as collecting biomedical readings, taking medicines, regulating diets, and doing regular physical activity.

Remote health monitoring has led to an improved quality of life, a higher efficiency, and an increased accessibility for healthcare professionals to patients with chronic diseases. For patients with chronic diseases, remote health monitoring systems provide remote sensing and data processing to make health status monitoring, data analysis, guidance, and emergency prevention available at home, without requiring the presence a full-time professional caregiver. These systems collect biomedical data that may be delivered to a central server for storage and analysis. This analysis is used centrally by caregivers to remotely monitor and assess their patients' health. If an abnormality in the patient's health is detected by the remote health monitoring system or noticed by a caregiver based on the information collected by the remote health monitoring system, the patient can be prompted to change a dose of a medication, to alter a level of physical activity, or to take other steps for addressing the abnormality. Such patient guidance can lead to significant improvements in patient health.

In the remote health monitoring domain, patients are required to perform daily tasks provided by their health care professionals. For many reasons, it may be desired to gather a large amount of data from a patient, and to provide many daily tasks to be performed. However, task complexity and difficulty can affect user participation and satisfaction. If a patient is presented too many tasks, it is more likely that the patient will skip some of the tasks or stop using the remote monitoring system altogether. Such system non-use can severely degrade the effectiveness of the designed system, and missing data can lead to biased and dangerous conclusions.

What is needed are techniques for reducing the number or complexity of tasks a patient must perform while nevertheless obtaining adequate monitored information from the patient to generate meaningful predictions about patient health.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a computer-implemented method of optimizing data collection tasks for patient monitoring is provided. A set of data collection tasks are performed by a computing device to obtain a set of monitoring data. The set of monitoring data is processed by a computing device to detect one or more association rules between two or more data collection tasks in the set of data collection tasks. The set of data collection tasks is optimized by a computing device based on the detected association rules. In some embodiments, a computer-readable medium is provided having computer-executable instructions stored thereon that, in response to execution by one or more processors of a computing device, cause the computing device to perform such a method.

In some embodiments, a system for patient monitoring is provided. The system for patient monitoring comprises a patient data processing system and a task optimization system. The patient data processing system and the task optimization system each include at least one computing device that comprises at least one processor and a memory. The at least one computing device of the patient data processing system is configured to retrieve a set of data collection tasks from a task data store; perform the set of data collection tasks to obtain a set of monitoring data; and store the set of monitoring data in a patient data store. The at least one computing device of the task optimization system is configured to retrieve the set of monitoring data from the patient data store; process the set of monitoring data to detect one or more association rules between two or more data collection tasks in the set of data collection tasks; optimize the set of data collection tasks based on the detected association rules; and store the optimized set of data collection rules in the task data store.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3 is a table that illustrates an acceptable range for blood glucose values and four questions that were presented along with their discrete answer value choices for a test of an embodiment of the present disclosure;

FIG. 4 is a table that illustrates discretized timestamp periods along with mean and standard deviation values of three different blood glucose levels for the test of the embodiment of the present disclosure;

FIG. 5 is a chart that illustrates a count of first order logic rules added for various time window values for the test of the embodiment of the present disclosure;

FIG. 6 is a table that illustrates a set of logic rules determined during the test of the embodiment of the present disclosure.

DETAILED DESCRIPTION

The present disclosure describes task optimization technology that combines data discretization methods and first-order logic to reduce patient burden in using remote health monitoring systems. Data mining techniques are applied to remote health monitoring systems in order to optimize data gathering tasks performed by patients. Optimized output of such a remote health monitoring system includes a minimal number of tasks which maximize information gain.

System Overview

Figure 1:
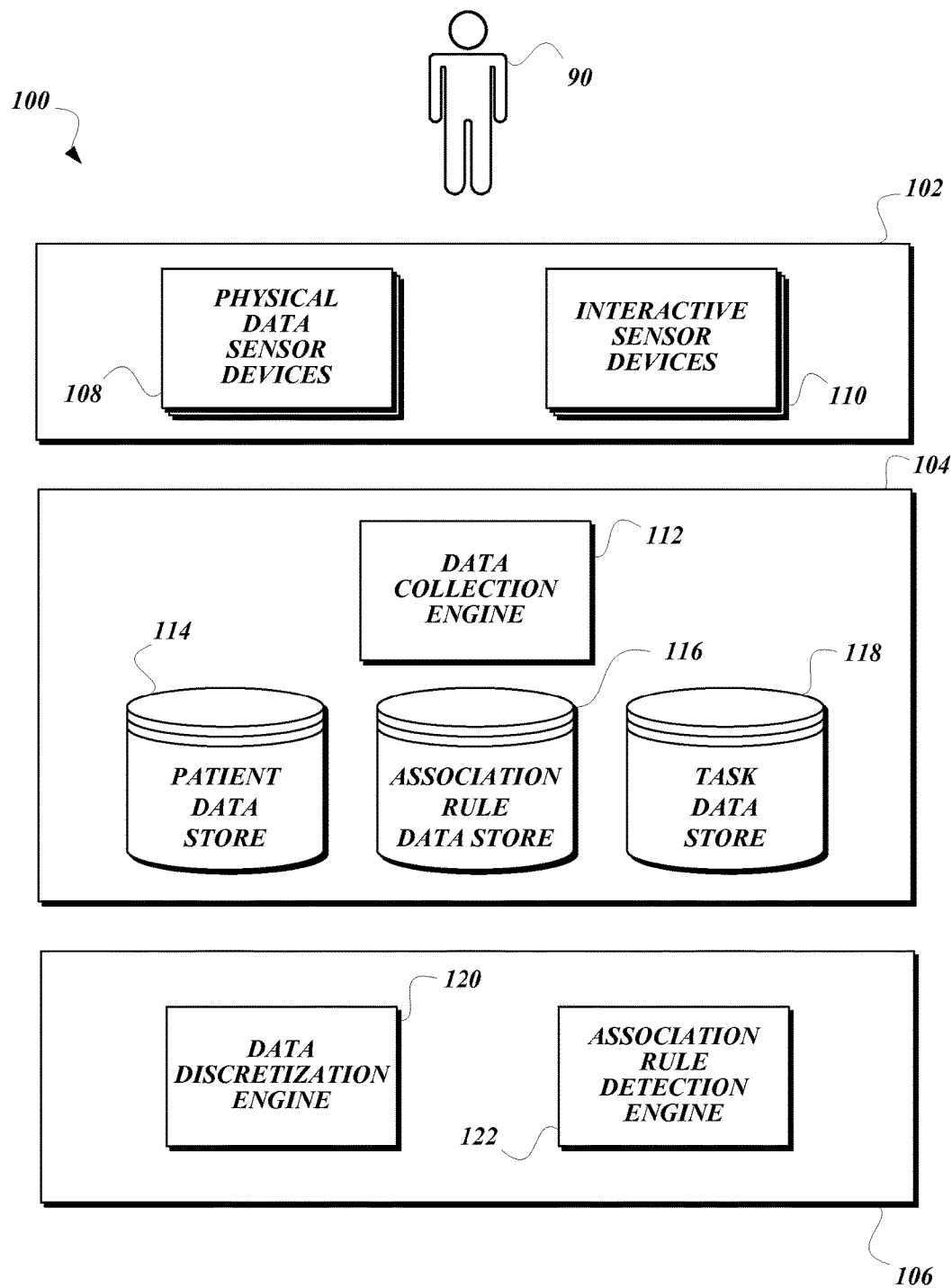
FIG. 1 is a block diagram that illustrates an exemplary embodiment of a remote health monitoring system according to various aspects of the present disclosure.
Figure 2A:
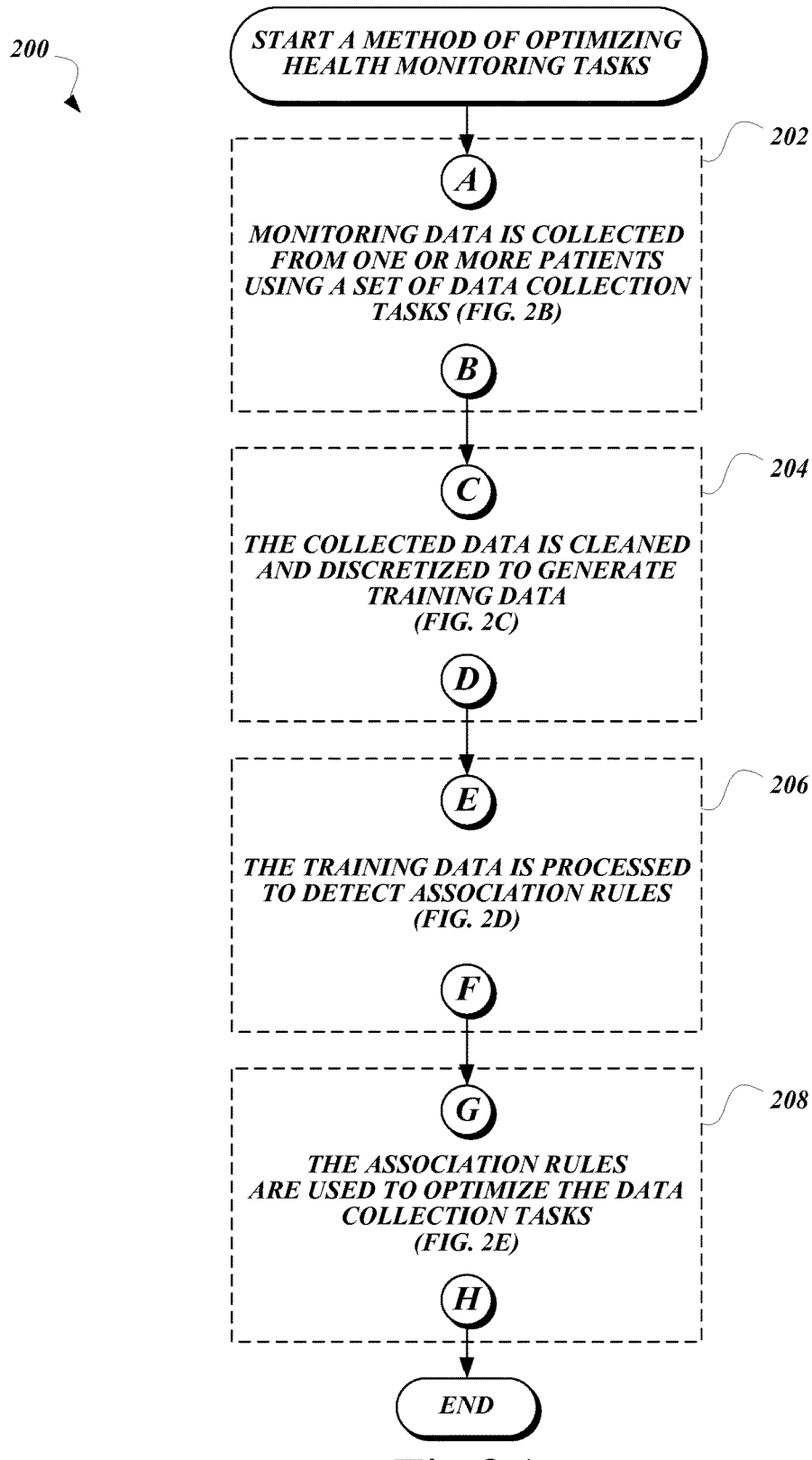
FIGS. 2A-2E are a flowchart that illustrates an exemplary embodiment of a method of optimizing health monitoring tasks according to various aspects of the present disclosure.
Figure 2B:
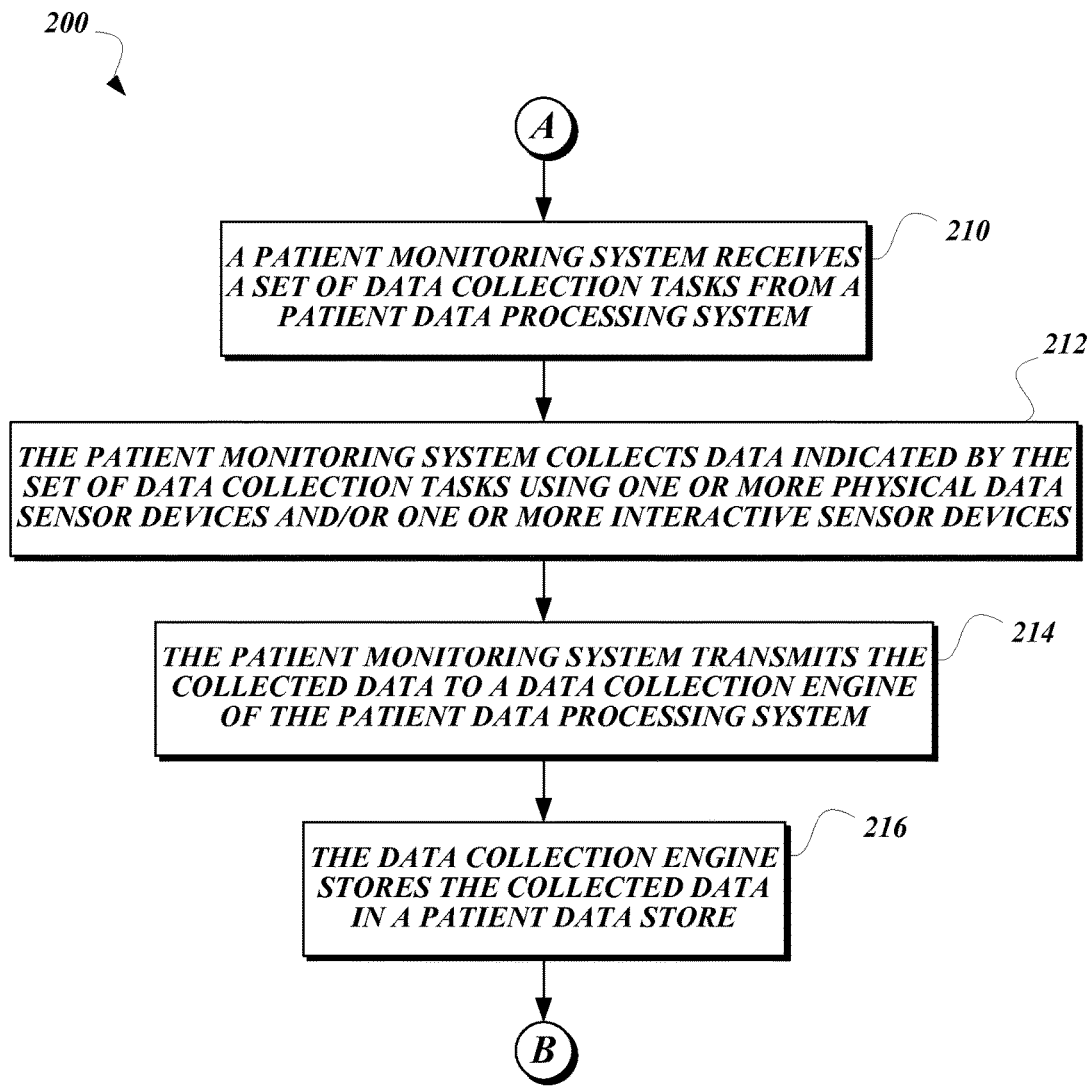
Figure 2C:
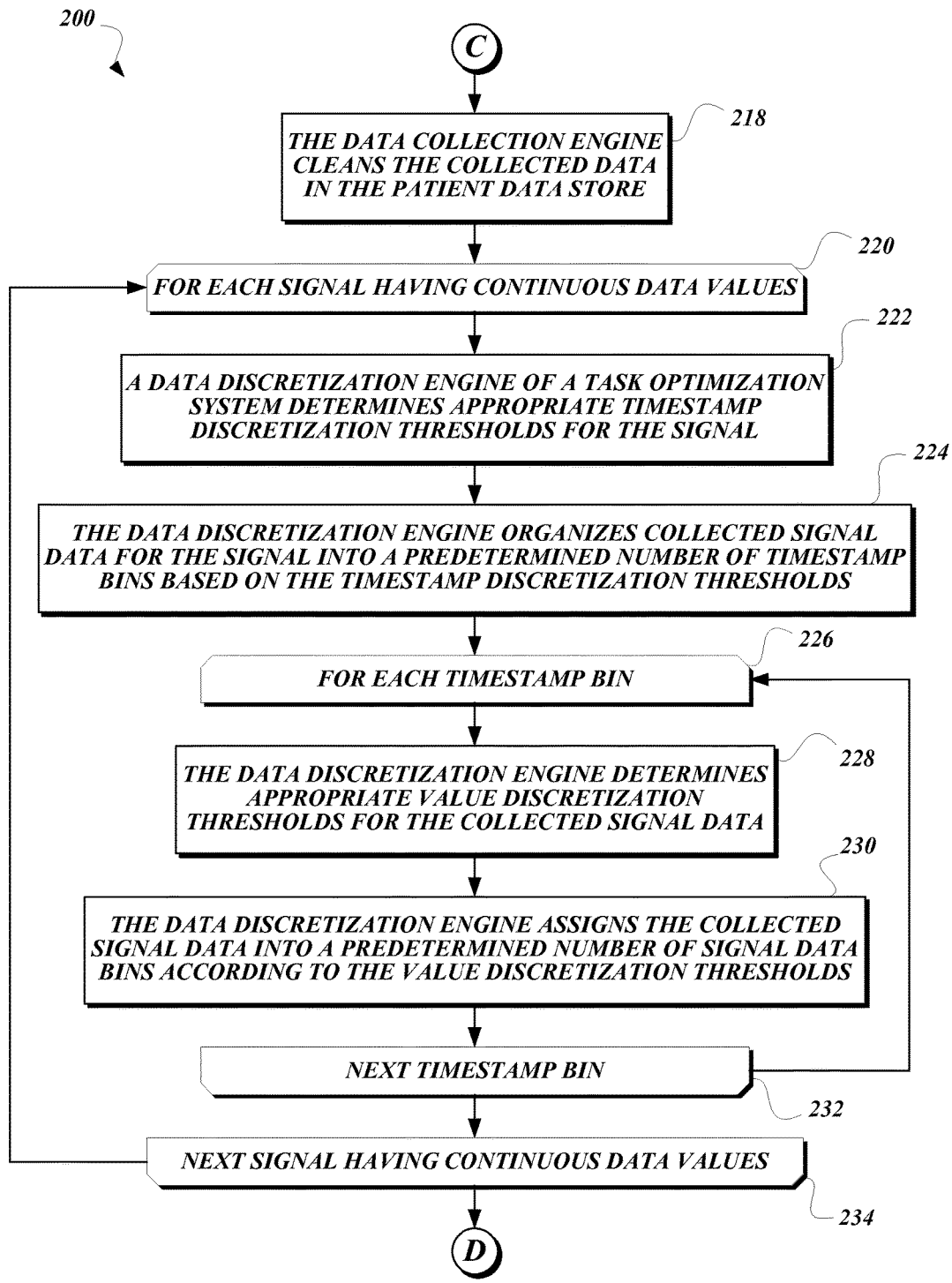
Figure 2D:
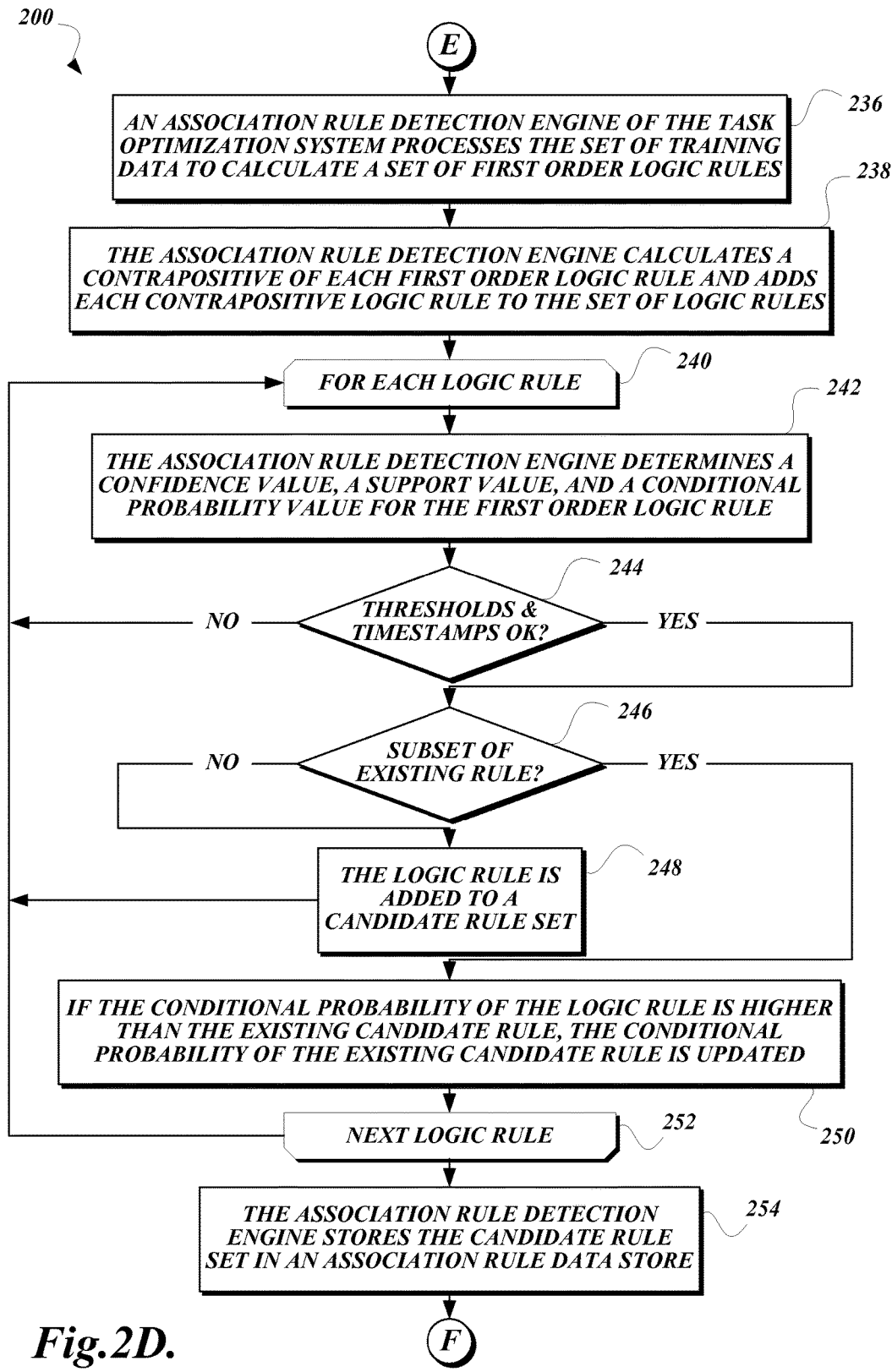
Figure 2E:
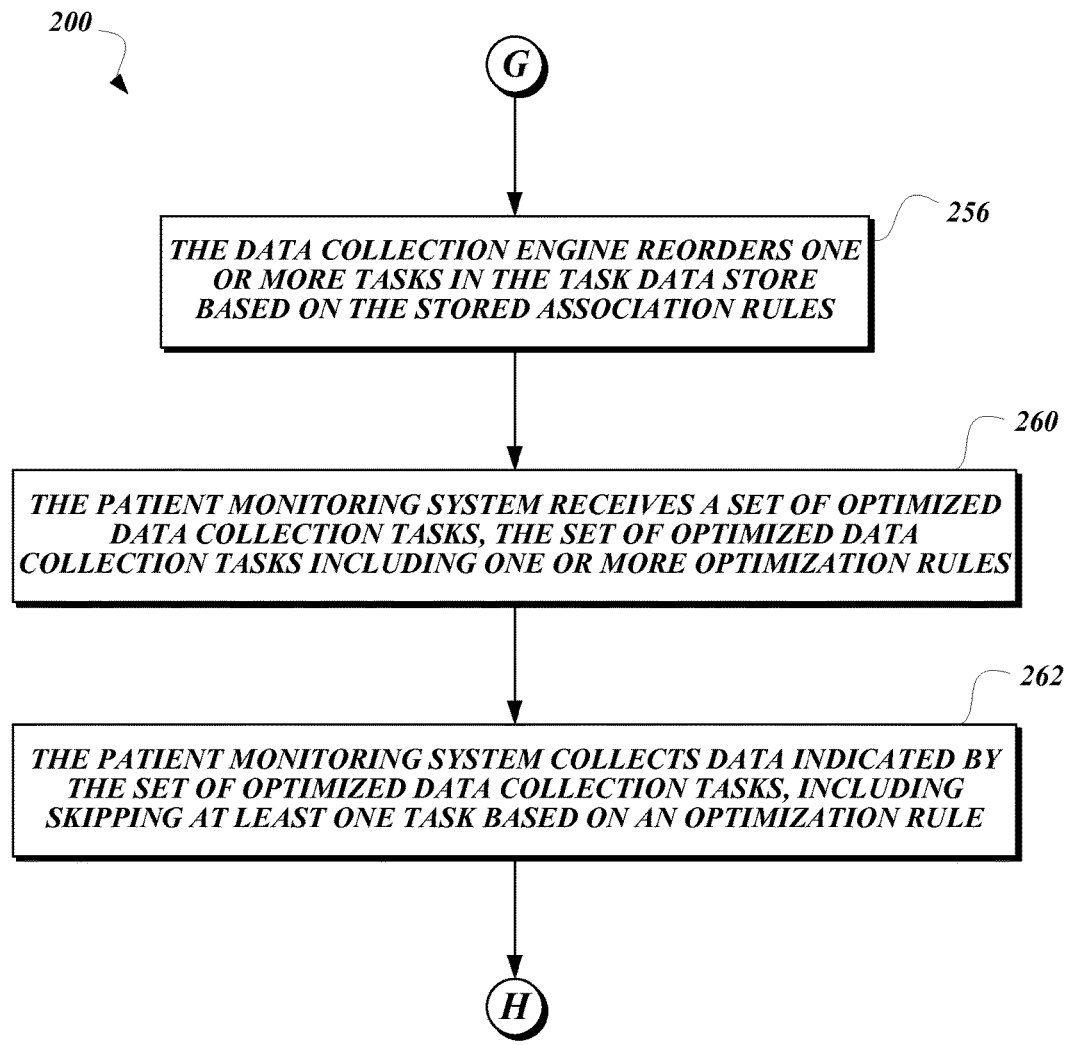

FIG. 1 is a block diagram that illustrates an exemplary embodiment of a remote health monitoring system 100 according to various aspects of the present disclosure. As illustrated, the remote health monitoring system 100 includes three tiers: a patient monitoring system 102, a patient data processing system 104, and a task optimization system 106. Each of the systems 102, 104, 106 may include one or more computing devices configured to provide the engines, data stores, and/or services illustrated and described herein as part of the respective system 102, 104, 106.

The patient data processing system 104 is configured to send one or more data collection tasks to the patient monitoring system 102, which cause the patient monitoring system 102 to collect particular measurements form the patient 90, and to transmit the collected information to the patient data processing system 104 for processing and storage. The task optimization system 106 is configured to access the collected information stored by the patient data processing system 104, to process the collected information to detect one or more association rules, and to use the detected association rules to optimize the data collection tasks.

In some embodiments, the patient monitoring system 102 may be located at the patient's home (or otherwise placed in a location easily accessible to the patient), while the patient data processing system 104 and the task optimization system 106 are placed in a central location such that multiple patient monitoring systems 102 in multiple locations may share the resources of a single patient data processing system 104 and/or task optimization system 106. In such embodiments, the components of the remote health monitoring system 100 may communicate with each other using any suitable communication technology, such as wired or wireless Internet communication, direct dial telephone or ISDN communication, and/or any other suitable communication technology. In some embodiments, the patient monitoring system 102, the patient data processing system 104, and/or the task optimization system 106 may be provided by a single computing device, or by multiple computing devices each located on the same network, thus obviating the need for long-distance communication between the elements of the system 100. Though FIG. 1 illustrates various components as being included in either the patient monitoring system 102, the patient data processing system 104, or the task optimization system 106, in some embodiments, the illustrated components may be moved from one of the illustrated systems 102, 104, 106 to another of the illustrated systems 102, 104, 106 or split between two or more of the illustrated systems 102, 104, 106; two or more of the illustrated systems 102, 104, 106 may be combined into a single system; and/or one of the illustrated systems 102, 104, 106 may be broken into multiple separate systems.

As illustrated, the patient monitoring system 102 includes one or more physical data sensor devices 108 and one or more interactive sensor devices 118 for collecting measurements from a patient 90. The physical data sensor devices 108 are physical devices that may automatically perform a measurement of a physical value, and may cause the detected physical value to be automatically transmitted to the patient data processing system 104 without further interaction from the patient 90. For example, the physical data sensor devices 108 may include, but are not limited to, an electronic sphygmomanometer, an electronic thermometer, an electronic heart rate monitor, a pedometer, an electronic scale, and/or the like. The interactive sensor devices 110 are physical devices that collect information entered by the patient 90 (or by a caregiver operating the patient monitoring system 102 on behalf of the patient 90). In some embodiments, an interactive sensor device 110 may be configured to present a prompt to the patient 90 to instruct the patient 90 to perform a measurement with a non-connected medical device or answer a survey question, and may subsequently allow the patient 90 to enter the result of the measurement or the answer the survey question. The interactive sensor device 110 then sends the collected information to the patient data processing system 104. In some embodiments, the interactive sensor devices 110 may include a desktop computing device executing a stand-alone application or presenting a web site, a mobile computing device such as a smart phone, a tablet computing device, a custom computing device configured to present an interface to the patient monitoring system 102, and/or the like.

As illustrated, the patient data processing system 104 includes a data collection engine 112. In general, the word "engine" (used interchangeably with the word application or module), as used herein, refers to logic embodied in hardware or software instructions, which may be written in a programming language, such as C, C++, COBOL, JAVA™, PHP, Perl, HTML, CSS, JavaScript, VBScript, ASPX, Microsoft.NET™, and/or the like. An engine may be compiled into executable programs or written in interpreted programming languages. Software engines or applications may be callable from other engines or from themselves. Generally, the engines or applications described herein refer to logical modules that can be merged with other engines or applications, or can be divided into sub-engines. The engines or applications may be stored in any type of computer-readable medium or computer storage device and be stored on and executed by one or more general purpose computers, thus creating a special purpose computer configured to provide the engine or application.

In some embodiments, the data collection engine 112 may provide a web service or other appropriate application programming interface (API) with which the patient monitoring system 102 communicates, such that data collection tasks may be transmitted to the patient monitoring system 102 and collected data may be received by the data collection engine 112 via the API. In some embodiments, the data collection engine 112 may generate a web-based interface to be presented to the patient 90 by the patient monitoring system 102 and into which the collected data may be directly entered. In some embodiments, the data collection engine 112 may cause the raw collected data to be stored, while in some embodiments, the data collection engine 112 may perform filtering or other data cleaning tasks before causing the collected data to be stored. Further functionality of the data collection engine 112 is described below.

The illustrated patient data processing system 104 also includes a patient data store 114, an association rule data store 116, and a task data store 118. As understood by one of ordinary skill in the art, a "data store" as described herein may be any suitable device configured to store data for access by a computing device. One example of a data store is a highly reliable, high-speed relational database management system (DBMS) executing on one or more computing devices and accessible over a high-speed packet switched network. However, any other suitable storage technique and/or device capable of quickly and reliably providing the stored data in response to queries may be used, and the computing device may be accessible locally instead of over a network, or may be accessible over some other type of suitable network or provided as a cloud-based service. A data store may also include data stored in an organized manner on a storage medium 708, as described further below. One of ordinary skill in the art will recognize that separate data stores described herein may be combined into a single data store, and/or a single data store described herein may be separated into multiple data stores, without departing from the scope of the present disclosure.

In some embodiments, the patient data store 114 is configured to store the data collected from the patient 90 by the patient monitoring system 102. In some embodiments, the patient data store 114 may also be configured to store other information related to patients, such as demographic information, associated health care provider information, login and password information, and/or the like. In some embodiments, the patient data store 114 may be configured to store data collected from the patient 90 as well as data that has been processed by the task optimization system 106.

In some embodiments, the association rule data store 116 is configured to store association rules detected by the task optimization system 106 based on the collected data. In some embodiments, the association rule data store 116 may also store information about each association rule indicating the rule's predictive strength, such as a confidence value, a support value, and/or a conditional probability value. The task data store 118 is configured to store data collection tasks. Each data collection task may include a unique identifier, one or more instructions for executing the task, and a set of response options. In some embodiments, the instructions may be directions for a patient 90 to conduct actions, while in some embodiments, the instructions may include computer-executable instructions for execution by a physical data sensor device 108. The unique identifiers of the data collection tasks may be used by the association rules in the association rule data store 116 to reference the data collection tasks. Further aspects of the patient data store 114, the association rule data store 116, and the task data store 118 are discussed below.

As illustrated, the task optimization system 106 includes a data discretization engine 120 and an association rule detection engine 122. In some embodiments, the data discretization engine 120 is configured to analyze collected data that includes continuous data values representing physiological measurements (i.e., signals that are values on a continuum such as a blood pressure value, a heart rate, a blood sugar reading, and/or the like, as opposed to discrete data such as multiple choice survey responses) in order to determine how the continuous data values may best be discretized. In some embodiments, the data discretization engine 120 may also be configured to clean the collected data before further processing. The association rule detection engine 122 is configured to analyze the collected data after it has been cleaned and discretized in order to detect association rules implied by the collected data and store the detected rules in the association rule data store 116. Further aspects of the data discretization engine 120 and the association rule detection engine 122 are described below.

Embodiments of the system 100 to optimize tasks are useful for improving participation rates in automated remote monitoring, at least because the system 100 may reduce the number of tasks a patient 90 is asked to perform. Also, in some embodiments, the system 100 may be operated by a caregiver, who may be located with the patient, or may instead be monitoring the patient remotely via telephone, via email, via text message, via video conference, or via any other suitable means. Even when operated by a caregiver, the reduction of tasks provided by the system 100 can be useful, at least because saving the caregiver time in attending to an individual patient can allow a single caregiver to render care to more patients overall.

Optimizing Tasks Using Association Rules

FIGS. 2A-2E are a flowchart that illustrates an exemplary embodiment of a method of optimizing health monitoring tasks according to various aspects of the present disclosure. Broadly speaking, the method 200 finds association rules between data collection tasks, and optimizes data collection tasks for execution to collect information from a patient. In some embodiments, data collection tasks are defined by domain experts to collect information from patients relevant to particular health conditions. For example, to remotely monitor the health of patients with diabetes, data collection tasks instructing a patient monitoring system 102 to collect blood pressure data, blood glucose measurement data, body weight data, and data including one or more survey question responses. As understood by one of ordinary skill in the art, other data may be automatically or interactively collected by the patient data monitoring system 102 to monitor patients with diabetes and/or other chronic conditions. Historical data from a set of patients is stored by the patient data processing system 104 and analyzed by the task optimization system 106 to optimize the set of data collection tasks, thereby increasing the likelihood of patient compliance while also maximizing information gain from the data collection tasks performed.

From a start block, the method 200 proceeds to a set of method steps 202 defined between a start terminal ("terminal A") and an exit terminal ("terminal B"), wherein monitoring data is collected from one or more patients using a set of data collection tasks. From terminal A (FIG. 2B), the method 200 proceeds to block 210, where a patient monitoring system 102 receives a set of data collection tasks from a patient data processing system 104. In some embodiments, the patient monitoring system 102 may request the set of data collection tasks from an API provided by a data collection engine 112 of the patient data processing system 104, and may be retrieved by the patient data processing system 104 from a patient data store 114. In some embodiments, the patient data store 114 may include sets of data collection tasks that are defined individually for each patient, while in some embodiments, the patient data store 114 may include sets of data collection tasks that are defined to be applicable to groups of patients being monitored for similar reasons. The set of data collection tasks may include an order in which the tasks are to be performed, and may include logic for choosing a subsequent task based on a value collected for an antecedent task. In embodiments wherein logic is included in the set of data collection tasks, the logic may initially not include any logic for skipping tasks until the method 200 has been performed.

Next, at block 212, the patient monitoring system 102 collects data indicated by the set of data collection tasks using one or more physical data sensor devices 108 and/or one or more interactive sensor devices 110, according to instructions included in each task of the set of data collection tasks and any logic provided with the set of data collection tasks. At block 214, the patient monitoring system 102 transmits the collected data to a data collection engine 112 of the patient data processing system 104. In some embodiments, the transmission of the collected data by the patient monitoring system 102 may occur automatically and without requiring further user interaction. As described above, the collected data may be transmitted to the patient data processing system 104 via the internet, a modem, a leased line, or via any other suitable communication technology. As also described above, in some embodiments the data collection engine 112 may provide a web service or other suitable API to receive the data from the patient monitoring system 102. At block 216, the data collection engine 112 stores the collected data in a patient data store 114. The method 200 then proceeds to terminal B.

In some embodiments, the set of method steps 202 described above may be performed multiple times to gather a set of data to be analyzed for task optimization. The repetition of the set of method steps 202 may be performed with a single patient over a period of time, or may be performed using data from many patients to provide greater statistical rigor for the conclusions drawn. In some embodiments, the data to be analyzed by the remainder of the method 200 may be collected using techniques other than those described in the set of method steps 202.

From terminal B (FIG. 2A), the method 200 proceeds to a set of method steps 204 defined between a start terminal ("terminal C") and an exit terminal ("terminal D"), wherein the collected data is cleaned and discretized to generate training data. From terminal C (FIG. 2C), the method 200 proceeds to block 218, where the data collection engine 112 cleans the collected data in the patient data store 114. The data cleaning may include detecting data that falls outside of predefined acceptable ranges (or automatically detected common ranges), detecting data that indicates system non-use, consolidating or disambiguating multiple measurements of the same value, and/or the like. In some embodiments, data cleaning may also include missing data imputation, such as techniques similar to those disclosed in commonly owned, co-pending International Patent Application No. PCT/US2012/052544, filed Aug. 27, 2012, which is hereby incorporated by reference herein in its entirety for all purposes. In some embodiments, the data cleaning may be performed on stored data, or may be performed while the data is being collected or otherwise at some point before the data is stored in the patient data store 114.

Many types of collected data may be signals that include continuous data values associated with timestamps. For example, a blood glucose level measurement may be a value on a continuum indicated by a number of milligrams per deciliter (mg/dL). Such a measurement may also be associated with a timestamp indicating a time of day at which the measurement was taken. Using the raw values of such data to optimize tasks may be possible, but in some embodiments, it may be desired to discretize the data to reduce the dimensionality and complexity of processing continuous data values. For example, a continuous blood glucose level measurement value may be discretized to be either a low value, a normal value, or a high value. Likewise, a timestamp value may be discretized to be either a morning, afternoon, or evening value.

Accordingly, the method 200 then proceeds to a for loop defined between a for loop start block 220 and a for loop end block 234. The for loop executes once for each signal to be analyzed from the collected data that includes continuous data values, and assigns a discrete value to the data according to the continuous data value. In some embodiments, a given signal may include both a measurement value and a timestamp value indicating when the measurement was taken. In such embodiments, the for loop discretizes both the measurement value and the timestamp value.

From the for loop start block 220, the method 200 proceeds to block 222, where a data discretization engine 120 of a task optimization system 106 determines appropriate timestamp discretization thresholds for the signal. In some embodiments, appropriate discretization thresholds could be predetermined by an expert, and the data discretization engine 120 may determine the thresholds by retrieving them from a data storage location. In some embodiments, optimal thresholds may be automatically determined using a data mining process. A number of bins and/or a number of thresholds may be predetermined by a user configuration, may be determined by an automatic iterative process, and/or using any other suitable manual or automatic technique.

One example of a data mining process for automated detection of optimal discretization thresholds includes the use of an expectation maximization (EM) algorithm. The use of the EM algorithm assumes that the collected sensor data follows a mixture of Gaussian distributions. The EM algorithm is an iterative method to optimize the estimation of an unknown parameter $\Theta$, given measured variables U and unmeasured variables J. The objective of the EM algorithm is the maximization of the posterior probability (Equation 1) of the parameter $\Theta$ given U and J.

$$\theta^* = \mathrm{argmax}_\theta \sum_J P(\theta, J|U) \quad (1)$$

The EM algorithm consists of two steps: The expectation step (E step) and the maximization step (M step). The E step finds a local lower-bound to the posterior distribution while the M step optimizes the bound obtained from the E step using iteration. In the E step, the algorithm calculates the expected value of the log likelihood function under the current estimate of the parameters $\Theta^t$ of the conditional distribution J given U. This step finds the best lower bound, $B(\Theta|\Theta^t)$.

$$B(\theta|\theta^t) = \sum_J \frac{f^t(J) \log P(U, J, \theta^t)}{f^t(J)} \text{ while} \quad (2)$$

$$f^t(J) = \frac{P(U, J, \theta^t)}{\sum_J P(U, J, \theta^t)} = P(J|U, \theta^t).$$

The M step iterates and chooses $\Theta t^{+1}$ by maximizing the bound, $B(\Theta|\Theta^t)$ from the E step.

$$\theta^{t+1} = \mathrm{argmax}_\theta B(\theta|\theta^t) = \mathrm{argmax}_\theta [Q^t(\theta)||\log P(\theta)] \quad (3)$$

while $Q^r(\Theta)$ is the expected complete log-likelihood, log $P(U,J|\Theta)$ and $P(\Theta)$ is the prior on the parameters $\Theta$. Based on mean and standard deviation values of each Gaussian curve from the EM algorithm, the method 200 finds intersection points and these points are used for automated discretization. As noted below in the test results, while some embodiments may use expert determination of discretization thresholds, automatically determined discretization thresholds determined using a technique such as the EM algorithm may produce more effective results.

Once appropriate timestamp discretization thresholds have been determined, the data discretization engine 120 organizes collected signal data for the signal into a predetermined number of timestamp bins based on the timestamp discretization thresholds, such that, for example, all of the "morning" readings are placed in a "morning bin," all of the "afternoon" readings are placed in an "afternoon bin," and all of the "evening" readings are placed in an "evening bin." The organization may be performed using any suitable method, such as adding a discrete value field to each measurement record in the patient data store 114 so that measurements from each bin may be quickly retrieved in response to queries, by copying each measurement in a given bin to a separate location associated with the given bin, and/or using any other suitable method. In some embodiments, the measurement data may not be further copied or updated, but instead the values that denote the cutoff points for each bin may be stored so that the measurements from each bin may be retrieved from the patient data store 114 using appropriately crafted database queries.

Once the signal measurements have been organized into timestamp bins, the method 200 proceeds to a for loop defined between a for loop start block 226 and a for loop end block 232. In the for loop, the measurement values within each timestamp bin are separately discretized. This may, for example, lead to similar values in different timestamp bins to be assigned different discrete values, depending on the distribution of continuous values within each timestamp bin. For example, a blood glucose reading of 167 mg/dL may be discretized as a low value in a first timestamp bin, while the same blood glucose reading may be discretized as a normal value in a second timestamp bin.

From the for loop start block 226, the method 200 proceeds to block 228, where the data discretization engine 120 determines appropriate value discretization thresholds for the collected signal data for the given timestamp bin. As discussed above, any suitable technique may be used for determining appropriate value discretization thresholds, such as expert determination, automated determination using the EM algorithm (or other algorithms, or any other suitable technique. At block 230, the data discretization engine assigns the collected signal data into a predetermined number of signal data bins according to the value discretization thresholds. Similar to the discussion above, the discretized signal data could be organized by copying to a new location, discrete values could be added to records in the patient data store 114, or could be organized using any other suitable technique.

The method 200 then proceeds to the for loop end block 232. If any further timestamp bins remain to be processed, the method 200 returns to the for loop start block 226 and processes the next timestamp bin. Otherwise, the method 200 proceeds to the for loop end block 234. If any further signals having continuous data values remain to be processed, the method 200 returns to the for loop start block 220 and processes the next signal. Otherwise, the method 200 has completed processing the collected signal data, and proceeds to terminal D.

The test results below show the benefits that can be gained from performing the method 200 as illustrated and described above. However, in other embodiments, discretization of timestamp and measurement values may be performed separately, such that measurement values are not first separated into timestamp bins before being discretized. In some embodiments, some signals may be processed differently from other signals, such as having thresholds determined by experts versus being determined automatically, being discretized according to timestamp bin or overall, and/or with any other difference.

Once the method 200 has completed the set of method steps 204, the collected signal data has been processed to generate training data. In some embodiments, the training data may include the collected signal data stored in the patient data store 114, after it has been altered to be cleaned and to include discretization values. In some embodiments, the training data may include a cleaned and discretized copy of the collected signal data separate from the original collected signal data, either stored in the patient data store 114 or stored in some other location accessible to the task optimization system 106.

From terminal D (FIG. 2A), the method 200 proceeds to a set of method steps 206 defined between a start terminal ("terminal E") and an exit terminal ("terminal F"), wherein the training data is processed to detect association rules. From terminal E (FIG. 2D), the method 200 proceeds to block 236, where an association rule detection engine 122 of the task optimization system 106 processes the set of training data to calculate a set of first order logic rules. In some embodiments, the Apriori algorithm is used to derive the set of first order logic rules. The discretized data are used in the algorithm as inputs and rules are derived by looking back a variable number of days (the "time window" discussed further below). The time window is increased by one day for each iteration of the Apriori algorithm. In some embodiments, the algorithm calculates the support and confidence of each implication so that the method 200 may choose implications meeting qualifying threshold limits (as discussed further below). In each subsequent pass, the large item sets found in the previous step may be used to generate the candidate sets (i.e., the largest item sets). The results of each step are large item sets of qualifying minimum support and confidence in the given time window.

Though time units of "days" are primarily discussed herein, this example is used for ease of discussion only. In some embodiments, the time window for which associations are sought may be measured in other units of time, such as weeks, months, hours, portion of day (e.g., morning, afternoon, evening, night), or any other suitable unit of time.

The Apriori algorithm operates substantially as follows: Let $I=\{i_1, i_2, \ldots i_m\}$ be a superset of all possible task outputs. Let D be a set of events such that D is a subset of I. An association rule is an implication of A implies B where A is a subset of I, B is a subset of I, and the intersection of A and B is empty. The algorithm also calculates a confidence value, a support value, and a conditional probability value for each association rule. Confidence c means that c % of events in D contain A and B. Support s indicates s % of events in D contain A or B. Conditional probability p indicates p % of events in D contain B when A happens. In some embodiments, these values may be stored along with the association rule to enable further filtering and processing of the association rules.

Next, at block 238, the association rule detection engine 122 calculates a contrapositive of each first order logic rule and adds each contrapositive logic rule to the set of logic rules. The contrapositive may also be generated during the execution of the Apriori algorithm along with the generation of the first order logic rules. The confidence, support, and conditional probability for the contrapositive logic rule are calculated from the set of training data similarly to the calculation of the same values for the first order logic rule as discussed above.

The method 200 then proceeds to a for loop defined between a for loop start block 240 and a for loop end block 252, wherein the set of logic rules is filtered down to a candidate rule set of association rules usable to optimize the tasks without losing significant information. In some embodiments, elements of the filter described in the for loop may be performed concurrently with the generation of first order logic rules discussed above with respect to block 236 or block 238, but is illustrated and discussed separately herein for ease of discussion. One of ordinary skill in the art will recognize that the filtering steps may be performed at any appropriate place in the overall method 200.

From the for loop start block 240, the method 200 proceeds to block 242, where the association rule detection engine 122 determines a confidence value, a support value, and a conditional probability value for the first order logic rule. In some embodiments, such values are determined by the rule generation algorithm, and the previously determined values are retrieved at this point. In some embodiments, such values may be determined by comparing the current rule to the other generated rules.

Next, the method 200 proceeds to a decision block 244, where a determination is made regarding whether thresholds and timestamps of the first order logic rule are OK. Regarding the thresholds, a predetermined confidence value threshold, a predetermined support value threshold, and a predetermined conditional probability value threshold may be established based on system settings. The confidence value, the support value, and the conditional probability value for the first order logic rule are compared to the corresponding thresholds to ensure that the candidate rules meet a minimum level of significance. Regarding the timestamps, a timestamp of the consequent of the first order logic rule is compared to a timestamp of the antecedent of the first order logic rule to ensure that the consequent occurs after the antecedent. If any of the thresholds are not met or if the consequent does not have a timestamp after a timestamp of the antecedent, the result of the determination at decision block 244 is NO, and the method 200 proceeds to the for loop start block 240 to process the next logic rule (if any) without adding the current first order logic rule to the candidate rule set.

Otherwise, if the thresholds are met and the consequent has a timestamp after a timestamp of the antecedent, the result of the determination at decision block 244 is YES, and the method 200 proceeds to a decision block 246. At decision block 246, a determination is made regarding whether the current first order logic rule is a subset of an existing rule already present in the candidate rule set. If the result of the determination at decision block 246 is NO, then the method 200 proceeds to block 248, where the logic rule is added to the candidate rule set. The method 200 then returns to the for loop start block 240 to process the next logic rule if any remain in the set of logic rules.

Otherwise, if the result of the determination at decision block 246 is YES, then the method 200 proceeds to block 250, where, if the conditional probability of the logic rule is higher than the conditional probability of the existing candidate rule, the conditional probability of the existing candidate rule is updated to match the conditional probability of the current logic rule. The method 200 then returns to the for loop start block 240 to process the next logic rule if any remain in the set of logic rules.

Once the for loop has processed all of the logic rules in the set of logic rules, the method 200 proceeds from the for loop end block 252 to block 254, where the association rule detection engine 122 stores the candidate rule set in an association rule data store 116. The method 200 then proceeds to terminal F.

From terminal F (FIG. 2A), the method 200 proceeds to a set of method steps between a start terminal ("terminal G") and an exit terminal ("terminal H"), wherein the association rules are used to optimize the data collection tasks. From terminal G (FIG. 2E), the method 200 proceeds to block 256, where the data collection engine 112 reorders one or more tasks in the task data store based on the stored association rules. As a nonlimiting example, if an association rule indicates that a given result to a first data collection task implies a result for a second data collection task, the first data collection task may be placed in order before the second data collection task. Next, at block 260, the patient monitoring system 102 receives a set of optimized data collection tasks, the set of optimized data collection tasks including one or more optimization rules. The method 200 then proceeds to block 262, where the patient monitoring system 102 collects data indicated by the set of optimized data collection tasks, including skipping at least one task based on an optimization rule. For example, if a first data collection task is performed and a given value is obtained that matches an antecedent of an association rule, one or more tasks indicated in the consequent of the association rule are subsequently skipped because the association rule can be used to infer the results of the skipped tasks. In some embodiments, the task skipping may be directed by logic added to the set of optimized data collection tasks, while in some embodiments the patient monitoring system 102 may use the optimization rules to dynamically detect when data collection tasks should be skipped. In some embodiments, the actions described with respect to block 262 may be performed using the same association rules and optimized tasks for more than one patient, and/or may be performed using the same association rules and optimized tasks multiple times for the same patient while the patient is being monitored. In some embodiments, the method 200 may be repeated in its entirety each time additional data is collected for a given patient, such that the latest data may be included with the previous training data for optimization and the overall training data set is kept up-to-date.

The method 200 then proceeds to terminal H, and then from terminal H (FIG. 2A) to an end block where the method 200 terminates.

Test Results

Embodiments of the above system and method have been verified in at least two studies performed to optimize remote health monitoring tasks for patients living with diabetes.

In a first study, participants eligible for recruitment were adults with Type 2 Diabetes having an HbA1c (a test that indicates how well the patient is controlling their diabetes) greater than or equal to 7.5, and who were recently hospitalized. Patients with active malignancy or those unable to provide informed consent were excluded, and patients were randomized to either intervention or control.

In the first study, data was used from 14 study participants assigned to the intervention arm, with an average participation duration of 59.67 days. Patients in the intervention arm were instructed to measure their blood sugar up to three times a day (morning, afternoon, and evening) and answer four survey questions per day. The defined acceptable ranges for blood glucose were between 80 and 200 mg/dL. The timestamp values were simply discretized as morning, afternoon, and evening based on an expert determination of appropriate value discretization thresholds for the timestamps. During the cleaning steps, missing data, multiple measurements, and out-of-normal-range values were noted. Existence of call logs between a patient and caregivers were also labeled. The data included 1688 instances, and each datum included 26 attributes. After data cleaning, 546 data points remained for analysis by the disclosed method.

The disclosed method was utilized with look back windows of one, two, and three days. With a one day look back window, 12 association rules were generated, with a minimum confidence of 0.97. With a two day look back window, two new rules were added, with a minimum confidence of 0.978. With a three day look back window, no new rules were added and the minimum confidence remained 0.978. Accordingly, it was determined that the two day look back window was optimal for the processed data.

Using the optimized rule set, the total number of patient tasks was reduced by an average of 28.6% with negligible information loss. Compared with Flach's algorithm (see Flach, P A. "Confirmation-guided discovery of first-order rules with Tertius." Machine learning, 42(½), 61-95. 2001), the embodiment of the present disclosure showed a higher confidence level (Flach's algorithm provided a maximum confidence level of 0.52 with a 1-3 day look back window) and higher efficiency.

A second study was performed using a larger data set, and to compare using expert determination of value discretization thresholds with the automatically determined value discretization thresholds described above. In the second study, participants eligible for recruitment were adults with Type 2 Diabetes having an HbA1c (a test that indicates how well the patient is controlling their diabetes) greater than or equal to 7.5, and who were recently hospitalized. Patients with active malignancy or those unable to provide informed consent were excluded, and patients were randomized to either intervention or control. Twenty-one study participants were assigned to the intervention arm, including 18 male participants and three female participants, with an average age of 48.13. Average participation duration was 52.23 days. Patients in the intervention arm were instructed to measure their blood sugar up to three times a day (morning, afternoon, and evening), and to answer four questions per day. FIG. 3 illustrates a table 300 that includes the acceptable range for blood glucose values and the four questions that were presented along with their discrete answer value choices.

During processing, the timestamps were discretized into three categories, and blood glucose values in each time category were also discretized into three levels. During cleaning, the collected data was indexed for missing data and multiple measurements, and the existence of call logs between a patient and caregivers were also labeled. The confidence value threshold and support threshold were set to 0.95, and the conditional probability threshold was set to 0.85. The total number of instances were 1117, and each datum included 54 attributes per day (including the patients' profile).

To find the best discretization method, different discretization approaches were applied using: 1) the experts' knowledge utilized in Hanefeld and Malherbe's studies (Hanefeld, M. Risk factors for myocardial infarction and death in newly detected NIDDM: the Diabetes Intervention Study, 11-year follow-up, Diabetologia, 39(12), 1577-1583, 1996; Malherbe, C. Circadian variations of blood sugar and plasma insulin levels in man, Diabetologia, 5(6), 397-404, 1969), on blood glucose and timestamp accordingly; 2) the EM algorithm; and 3) the combination of experts' knowledge and the EM algorithm.

For experts' knowledge-based discretzation (EKTBD), timestamps were categorized into three different time periods (Ti), and blood glucose readings were also categorized into three different levels. Each timestamp period is T1: 7:30:00-12:00:00, T2: 12:00:00-16:30:00 and T3: 16:30:00-21:00:00; and each blood glucose level is B1: <80 mg/dl, B2: 80-200 mg/dl and B3:>200 mg/dl.

For discretizing timestamps only (EMTD), the EM algorithm was applied on collected timestamps of blood glucose measurements, and experts' knowledge was applied on blood glucose readings. Timestamps were discretized as T1: 0:00:00-8:29:59, T2: 8:29:59-15:09:45 and T3: 15:09:45-23:59:59; and blood glucose readings were discretized as B1: <80 mg/dl, B2: 80-200 mg/dl and B3: >200 mg/dl.

For discretizing blood glucose only (EMBD), the EM algorithm was utilized on collected blood glucose readings, and experts' knowledge was applied on timestamps. Each timestamp period is T1: 7:30:00-12:00:00, T2: 12:00:00-16:30:00 and T3: 16:30:00-21:00:00; and blood glucose readings were categorized as B1: <170.8 mg/dl, B2: 170.8-274.0 mg/dl and B3: >274.0 mg/dl.

For quantizing both timestamps and blood glucose readings (EMTBD), the EM algorithm was utilized on collected timestamps of blood glucose measurements to discretize data into three timestamp bins, and readings collected in each time period were further discretized into three levels. In other words, using the method 200 described above, each time interval was assigned different discretization thresholds, and therefore used different standards of categorizing blood glucose data in three different levels. Each discretized timestamp period, as well as mean and standard deviation values of its three different blood glucose levels are listed in the table 400 illustrated in FIG. 4. An assumption was made that the readings were a mixture of Gaussian distributions, and the intersections of Gaussian curves were found. The obtained B1, B2, B3 ranges of T1 (B11, B12, B13) were <166, 166-372, and >372. B21, B22, B23, B31, B32, B33 were <169, 169-265, >265; and <185, 185-318, >318 mg/dL accordingly.

The experimental results show that the maximum sliding window size to make the conditional probabilities of ten best Apriori first order logic rules 1.00 is 4 days in EMTBD, while other methods require 5 days. Therefore, the method 200 described above has been shown reduce the required time windows to 4 days to reach the maximum conditional probability, while utilizing experts' knowledge requires 5 days worth of data to reach the same conditional probability. Furthermore, discretizing timestamp and quantizing blood glucose data of each time frame using the EM algorithm yields less computational power and maximizes information gain in a shorter period of time compared to using experts' knowledge-based methods.

Moving on to association rule mining, FIG. 5 illustrates a chart 500 that shows a count of first order logic rules added for various time window values. The proposed algorithm had optimal results with a look back window of 5 days. The minimum confidence peaks at 1.00 at 2 to 5 days. Compared to the first study which utilizes experts' knowledge for discretization, the combination of EM algorithm-based discretization and the Apriori algorithm for detecting association rules shows improvement of 1.292% of minimum confidence.

The chart 500 shows the number of new rules added or updated with increasing window size. A total of 7 rules were added with a window size of one day and a total of 19 rules were updated with a window size of 5 days. No rules were added or updated with a look-back window of more than 5 days. Compared with the first study, a larger amount of data (546 data in the first study versus 1117 data in this study after data cleaning) and the EM algorithm-based discretization yields more rules with larger size of sliding window from the Apriori algorithm. The total number of patient tasks was reduced by up to 76.19% with negligible information loss. For example, as shown in the table 600 in FIG. 6, it was found that responses to Q3 and Q4 can be inferred from each other.

Although the two studies described above relate to remote monitoring of patients with diabetes, one of ordinary skill in the art will recognize that the techniques described above can easily be adapted to optimize monitoring tasks for any other health condition that is monitored remotely. As non-limiting examples, patients with chronic heart failure, patients with sleep apnea, patients with COPD, and patients with hypertension may all be monitored in similar ways to those described above. That is, for each of these conditions, the patient may be instructed to periodically answer one or more survey questions, and/or may be instructed to periodically provide a physical measurement (such as a blood pressure reading, a blood glucose level, motion/activity detection, and/or the like). For any of these conditions or any other condition that uses similar remote monitoring, the techniques described above can be used to optimize the data collection tasks without undue experimentation.

Exemplary Computing Device

Figure 7:
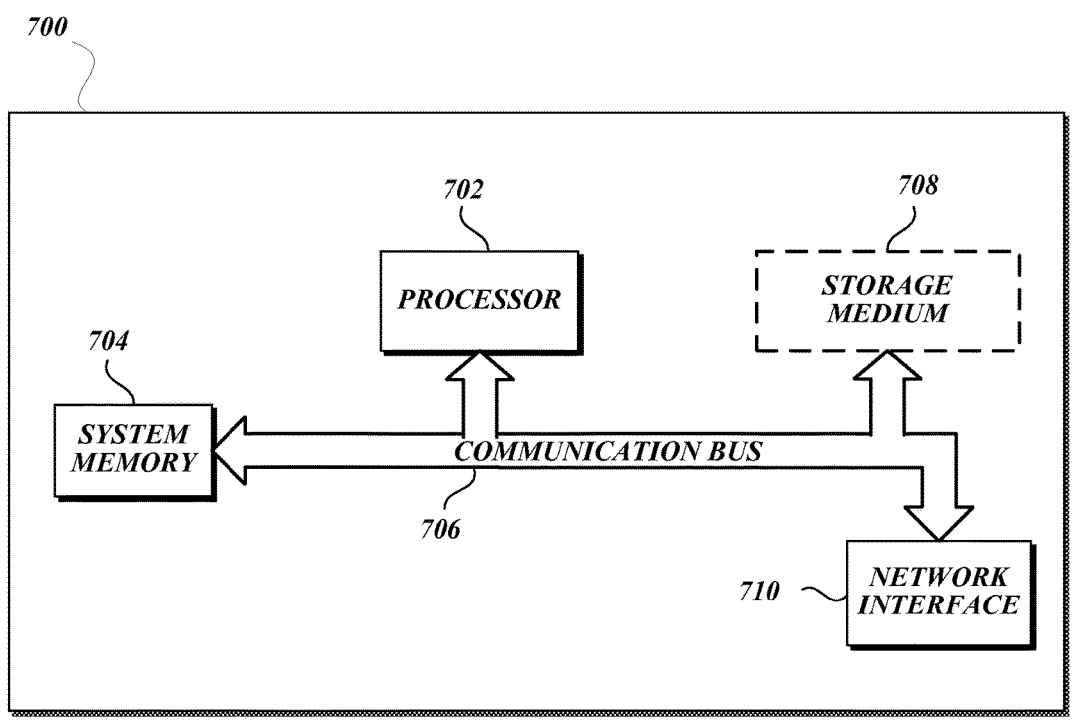
FIG. 7 is a block diagram that illustrates aspects of an exemplary computing device appropriate for use with embodiments of the present disclosure.

FIG. 7 is a block diagram that illustrates aspects of an exemplary computing device 700 appropriate for use with embodiments of the present disclosure. While FIG. 7 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 700 may be any one of any number of currently available or yet to be developed devices.

In its most basic configuration, the computing device 700 includes at least one processor 702 and a system memory 704 connected by a communication bus 706. Depending on the exact configuration and type of device, the system memory 704 may be volatile or nonvolatile memory, such as read only memory ("ROM"), random access memory ("RAM"), EEPROM, flash memory, or similar memory technology. Those of ordinary skill in the art and others will recognize that system memory 704 typically stores data and/or program modules that are immediately accessible to and/or currently being operated on by the processor 702. In this regard, the processor 702 may serve as a computational center of the computing device 700 by supporting the execution of instructions.

As further illustrated in FIG. 7, the computing device 700 may include a network interface 710 comprising one or more components for communicating with other devices over a network. Embodiments of the present disclosure may access basic services that utilize the network interface 710 to perform communications using common network protocols. The network interface 710 may also include a wireless network interface configured to communicate via one or more wireless communication protocols, such as WiFi, 2G, 3G, LTE, WiMAX, Bluetooth, and/or the like.

In the exemplary embodiment depicted in FIG. 7, the computing device 700 also includes a storage medium 708. However, services may be accessed using a computing device that does not include means for persisting data to a local storage medium. Therefore, the storage medium 708 depicted in FIG. 7 is represented with a dashed line to indicate that the storage medium 708 is optional. In any event, the storage medium 708 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 704 and storage medium 708 depicted in FIG. 7 are merely examples of computer-readable media.

Suitable implementations of computing devices that include a processor 702, system memory 704, communication bus 706, storage medium 708, and network interface 710 are known and commercially available. For ease of illustration and because it is not important for an understanding of the claimed subject matter, FIG. 7 does not show some of the typical components of many computing devices. In this regard, the computing device 700 may include input devices, such as a keyboard, keypad, mouse, microphone, touch input device, touch screen, tablet, and/or the like. Such input devices may be coupled to the computing device 700 by wired or wireless connections including RF, infrared, serial, parallel, Bluetooth, USB, or other suitable connections protocols using wireless or physical connections. Similarly, the computing device 700 may also include output devices such as a display, speakers, printer, etc. Since these devices are well known in the art, they are not illustrated or described further herein.

As will be appreciated by one skilled in the art, the specific routines described above in the flowcharts may represent one or more of any number of processing strategies such as event-driven, interrupt-driven, multi-tasking, multi-threading, and the like. As such, various acts or functions illustrated may be performed in the sequence illustrated, in parallel, or in some cases omitted. Likewise, the order of processing is not necessarily required to achieve the features and advantages, but is provided for ease of illustration and description. Although not explicitly illustrated, one or more of the illustrated acts or functions may be repeatedly performed depending on the particular strategy being used. Further, these FIGURES may graphically represent code to be programmed into a computer readable storage medium associated with a computing device.

While illustrative embodiments have been illustrated and described, it will be appreciated that various changes can be made therein without departing from the spirit and scope of the claimed subject matter.

The invention claimed is:

1. A computer-implemented method of optimizing data collection tasks for patient monitoring, the method comprising:

performing, by a first computing device, a set of data collection tasks to obtain a set of monitoring data, the set of monitoring data comprising sensor data measured from a patient;

processing, by the first computing device or a second computing device, the set of monitoring data to detect one or more association rules between two or more data collection tasks in the set of data collection tasks, wherein processing the set of monitoring data includes:
   determining a candidate set of first order logic rules based on the set of monitoring data, and
   for each first order logic rule in the candidate set of first order logic rules:
      in response to determining that a timestamp of a consequent of the first order logic rule is larger than a timestamp of an antecedent of the first order logic rule, and that an implication of the first order logic rule is not a subset of any rules in the detected one or more association rules, adding the first order logic rule to the detected one or more association rules;

optimizing, by the first computing device or the second computing device, the set of data collection tasks based on the detected association rules, wherein optimizing the set of data collection tasks includes:
   in response to a data collection task in the set of data collection tasks is performed to obtain a value that matches an antecedent of an association rule in the detected one or more association rules, skipping one or more data collection tasks indicated as a consequent of the association rule; and continuing obtaining an additional set of monitoring data by performing the optimized set of data collection tasks by the first computing device.

2. The computer-implemented method of claim 1, wherein processing the set of monitoring data to detect one or more association rules between two or more data collection tasks in the set of data collection tasks includes discretizing at least one signal having continuous data values included in the set of monitoring data.

3. The computer-implemented method of claim 2, wherein discretizing at least one signal having continuous data values included in the set of monitoring data comprises:
   determining discretization thresholds for timestamps assigned to the at least one signal to cluster the associated data into a predetermined number of timestamp bins; and
   determining discretization thresholds for continuous data values of the at least one signal for each timestamp bin to cluster the associated continuous data values into a predetermined number of signal data bins for each timestamp bin.

4. The computer-implemented method of claim 3, wherein determining discretization thresholds includes utilizing expectation maximization.

5. The computer-implemented method of claim 1, wherein processing the set of monitoring data to detect one or more association rules between two or more data collection tasks in the set of data collection tasks includes:
   calculating a set of first order logic rules implied by the set of monitoring data;
   and wherein determining a candidate set of first order logic rules based on the set of monitoring data includes:
      determining the candidate set of first order logic rules of the set of first order logic rules that have a confidence value greater than a confidence value threshold, a support value greater than a support value threshold, and a conditional probability value greater than a conditional probability value threshold.

6. The computer-implemented method of claim 5, wherein processing the set of monitoring data to detect one or more association rules between two or more data collection tasks in the set of data collection tasks further includes:
   calculating at least one contrapositive logic rule based on at least one first order logic rule in the candidate set of first order logic rules; and
   adding the contrapositive logic rule to the candidate set of first order logic rules.

7. The computer-implemented method of claim 5, wherein processing the set of monitoring data to detect one or more association rules between two or more data collection tasks in the set of data collection tasks further includes:
   for each first order logic rule in the candidate set of first order logic rules:
      in response to determining that a timestamp of a consequent of the first order logic rule is larger than a timestamp of an antecedent of the first order logic rule, that an implication of the first order logic rule is a subset of a detected rule in the detected one or more association rules, and that the first order logic rule has a higher conditional probability than the detected rule, updating the detected rule with the higher conditional probability of the first order logic rule.

8. The computer-implemented method of claim 5, wherein optimizing the set of data collection tasks includes reordering the data collection tasks in the set of data collection tasks based on the detected association rules to increase a likelihood that a result of a subsequent task is implied by a result of a precedent task.

9. The computer-implemented method of claim 1, wherein performing a set of data collection tasks includes obtaining a value representing a physical measurement obtained by a physical data sensor device.

10. The computer-implemented method of claim 1, wherein performing a set of data collection tasks includes:
   presenting a question to a patient using an interactive sensor device; and
   receiving a response to the question using the interactive sensor device.

11. The computer-implemented method of claim 1, further comprising inferring, by the first computing device or the second computing device, results of the skipped one or more data collection tasks from the association rule in the detected one or more association rules.

12. A system for patient monitoring, comprising:
   a patient data processing system including at least one computing device, wherein the at least one computing device comprises at least one processor and a memory, and wherein the at least one computing device is configured to:
      retrieve a set of data collection tasks from a task data store;
      perform the set of data collection tasks to obtain a set of monitoring data, the set of monitoring data comprising sensor data measured from a patient; and
      store the set of monitoring data in a patient data store; and
   a task optimization system including at least one computing device, wherein the at least one computing device comprises at least one processor and a memory, and wherein the at least one computing device is configured to:

retrieve the set of monitoring data from the patient data store;
process the set of monitoring data to detect one or more association rules between two or more data collection tasks in the set of data collection tasks, wherein the at least one computing device is further configured to:
determine a candidate set of first order logic rules based on the set of monitoring data, and
for each first order logic rule in the candidate set of first order logic rules:
in response to determining that a timestamp of a consequent of the first order logic rule is larger than a timestamp of an antecedent of the first order logic rule, and that an implication of the first order logic rule is not a subset of any rules in the detected one or more association rules, add the first order logic rule to the detected one or more association rules;
optimize the set of data collection tasks based on the detected association rules; and
store the optimized set of data collection tasks in the task data store;
wherein the at least one computing device included in the patient data processing system is further configured to obtain an additional set of monitoring data by performing the optimized set of data collection tasks.

13. The system of claim 12, wherein processing the set of monitoring data to detect one or more association rules between two or more data collection tasks in the set of data collection tasks includes discretizing at least one signal having continuous data values included in the set of monitoring data.

14. The system of claim 13, wherein discretizing at least one signal having continuous data values included in the set of monitoring data comprises:
determining discretization thresholds for timestamps assigned to the at least one signal to cluster the associated data into a predetermined number of timestamp bins; and
determining discretization thresholds for continuous data values of the at least one signal for each timestamp bin to cluster the associated continuous data values into a predetermined number of signal data bins for each timestamp bin.

15. The system of claim 14, wherein determining discretization thresholds includes utilizing expectation maximization.

16. The system of claim 12, wherein processing the set of monitoring data to detect one or more association rules between two or more data collection tasks in the set of data collection tasks includes:
calculating a set of first order logic rules implied by the set of monitoring data;
determining a candidate set of first order logic rules of the set of first order logic rules that have a confidence value greater than a confidence value threshold, a support value greater than a support value threshold, and a conditional probability value greater than a conditional probability value threshold; and
for each first order logic rule in the candidate set of first order logic rules:
in response to determining that a timestamp of a consequent of the first order logic rule is larger than a timestamp of an antecedent of the first order logic rule, and that an implication of the first order logic rule is not a subset of any rules in the detected one or more association rules, adding the first order logic rule to the detected one or more association rules.

17. The system of claim 16, wherein processing the set of monitoring data to detect one or more association rules between two or more data collection tasks in the set of data collection tasks further includes:
calculating at least one contrapositive logic rule based on at least one first order logic rule in the candidate set of first order logic rules; and
adding the contrapositive logic rule to the candidate set of first order logic rules.

18. The system of claim 16, wherein processing the set of monitoring data to detect one or more association rules between two or more data collection tasks in the set of data collection tasks further includes:
for each first order logic rule in the candidate set of first order logic rules:
in response to determining that a timestamp of a consequent of the first order logic rule is larger than a timestamp of an antecedent of the first order logic rule, that an implication of the first order logic rule is a subset of a detected rule in the detected one or more association rules, and that the first order logic rule has a higher conditional probability than the detected rule, updating the detected rule with the higher conditional probability of the first order logic rule.

19. The system of claim 16, wherein optimizing the set of data collection tasks includes reordering the data collection tasks in the set of data collection tasks based on the detected association rules to increase a likelihood that a result of a subsequent task is implied by a result of a precedent task.

20. The system of claim 12, further comprising at least one physical data sensor device, and wherein performing a set of data collection tasks includes obtaining a value representing a physical measurement obtained by the at least one physical data sensor device.

21. The system of claim 12, further comprising at least one interactive sensor device, and wherein performing a set of data collection tasks includes:
presenting a question to a patient using the interactive sensor device; and
receiving a response to the question using the interactive sensor device.

22. The system of claim 12, wherein optimizing the set of data collection tasks includes:
in response to a data collection task in the set of data collection tasks is performed to obtain a value that matches an antecedent of an association rule in the detected one or more association rules, skipping one or more data collection tasks indicated as a consequent of the association rule.

23. A non-transitory computer-readable medium having computer-executable instructions stored thereon that, in response to execution by one or more processors of a computing device, cause the computing device to perform the method as recited in claim 1.

* * * * *